United States Patent [19]

Siwajek et al.

[11] Patent Number: 5,681,360
[45] Date of Patent: Oct. 28, 1997

[54] LANDFILL GAS RECOVERY

[75] Inventors: Lawrence A. Siwajek, Bentleyville; W. Jeffrey Cook, Cleveland Heights; William R. Brown, Brecksville, all of Ohio

[73] Assignee: Acrion Technologies, Inc., Valley View, Ohio

[21] Appl. No.: 371,136

[22] Filed: Jan. 11, 1995

[51] Int. Cl.$^6$ ............................................. C01B 3/32
[52] U.S. Cl. ................. 48/127.3; 48/127.5; 48/198.3; 48/197 A; 95/42; 95/149; 95/229
[58] Field of Search ........................ 48/127.3, 127.5, 48/198.3, 197 A; 62/17; 95/42, 149, 229

[56] References Cited

U.S. PATENT DOCUMENTS

| | | | |
|---|---|---|---|
| H825 | 10/1990 | Green et al. ........................... | 62/20 |
| 4,270,937 | 6/1981 | Adler et al. ........................... | 62/17 |
| 4,371,381 | 2/1983 | Schuftan ............................... | 55/27 |
| 4,417,449 | 11/1983 | Hegarty et al. ........................ | 62/28 |
| 4,449,994 | 5/1984 | Hegarty et al. ........................ | 62/17 |
| 4,475,347 | 10/1984 | Hegarty et al. ........................ | 62/17 |
| 4,563,202 | 1/1986 | Yao et al. ............................. | 62/17 |
| 4,609,384 | 9/1986 | Ranke et al. .......................... | 55/40 |
| 4,681,612 | 7/1987 | O'Brien et al. ........................ | 62/23 |
| 4,720,294 | 1/1988 | Lucadamo et al. .................... | 62/31 |

*Primary Examiner*—Timothy McMahon
*Attorney, Agent, or Firm*—Pearne, Gordon, McCoy & Granger LLP

[57] ABSTRACT

A process for concentrating and recovering methane and carbon dioxide from landfill gas includes absorption of commonly occurring pollutants using a reduced amount of carbon dioxide absorbent which itself may be an in situ derived and recoverable constituent. Separated methane may be concentrated into a high heating value fuel, and a highly pure food-grade carbon dioxide product may also be recovered. Process streams may be used to provide fuel for compression and refrigeration and/or to regenerate carbon dioxide absorbent.

33 Claims, 3 Drawing Sheets

5,681,360

LANDFILL GAS RECOVERY

BACKGROUND OF THE INVENTION AND RELATED ART

This invention generally relates to the separation and recovery of methane and carbon dioxide from landfill gas. More particularly, the invention provides an improved process for concentrating and removing commonly occurring pollutants from landfill gas using a reduced amount of carbon dioxide absorbent which itself may be an in situ derived and recoverable constituent. The separated methane may be concentrated into a high pressure, high heating value fuel which is suitable for use with motors or vehicle engines adapted to be fueled by compressed or liquified natural gas, and a highly pure food-grade carbon dioxide product may also be recovered from the landfill gas. Process streams may be used to provide fuel for compression and refrigeration and/or to regenerate absorbent added to The process for further separation of methane and carbon dioxide.

The landfill gas may be generated by the decomposition of buried waste or garbage and is principally comprised of methane and carbon dioxide together with minor amounts of nitrogen, oxygen, hydrogen, carbon monoxide and a variety of trace contaminants. As used herein, the landfill gas contains methane and carbon dioxide in mole percents ranging from about 35% to 65% for each constituent, a combined nitrogen and oxygen content of less than about 10% and trace contaminants that may vary widely in type and amount so as to make uniform processing and/or equipment a difficult task to achieve economically. Typical contaminants include hydrocarbons other than methane, halocarbons, oxygenated and sulfur containing hydrocarbons, hydrogen sulfide and carbon monoxide.

Because of its high methane content, landfill gas has attracted much attention as a potential fuel gas. However, in order to utilize landfill gas as a substitute for natural gas in existing fuel distribution systems or as a fuel for internal combustion engines, it is necessary to remove carbon dioxide to raise the heating value of the gas to an acceptable level and to substantially remove the contaminants in a competitively economical manner. This task is especially complicated by the variations in contaminant types and amounts encountered in various landfill gases as well as the gases obtained from a single landfill over a period of time or at different locations in the landfill. For example, the processing of a landfill gas containing no hydrogen sulfide may be significantly simplified and less expensive processing operation as compared with a landfill gas containing a hydrogen sulfide contaminant.

Gas separation contemplates a wide range of technologies with varying capital and processing cost effects. Known processes for the separation of carbon dioxide from other gases include refrigeration to cause solid carbon dioxide formation, adsorption by molecular sieves to capture carbon dioxide, contacting the gases with a solvent capable of selectively absorbing carbon dioxide, separation of methane from carbon dioxide using semi-permeable membranes, or a combination of such techniques. These known processes for separating carbon dioxide from landfill gas are generally prohibitively expensive, do not facilitate recovery of carbon dioxide, and/or permit the potential presence of trace contaminants in the methane fuel.

Absorbents, such as amines and other commonly used organic solvents, often react with trace contaminants which are generally present in landfill gas to produce compounds which foam, become viscous, or otherwise impair the effectiveness of the absorbent. Even chemically inert organic solvents are difficult to regenerate once contaminated because of similarities in the physical and chemical properties of the solvents and contaminants. Absorbents which cannot be fully regenerated continue to accumulate trace contaminants until the absorbent becomes saturated and the contaminants break through with the fuel product. Consequently, absorption processes often have the disadvantages of routinely requiring fresh solvent and have the potential for permitting toxic contaminants to become present in the fuel product. Moreover, absorption processes do not facilitate economically feasible recovery of the carbon dioxide, which must instead be incinerated in a stream containing the trace contaminants.

Adsorption processes have many disadvantages similar to those of absorption processes. In particular, trace contaminants from the landfill gas can become permanently bound to the molecular sieve adsorbent causing fouling and blocking of adsorption sites, thereby increasing the pressure drop across the adsorption column and/or causing loss of capacity. Eventually, sufficient quantities of impurities can accumulate to prevent effective regeneration of the adsorbent and there is also the potential for breakthrough of toxic impurities to the fuel product. Consequently, as with absorbent solvents, fresh adsorbent will be required periodically.

Membrane separation processes for removing carbon dioxide also have many disadvantages. With membrane separations, a significant portion of the methane is not recovered, and carbon dioxide recovery is not economically feasible which means that the carbon dioxide stream containing the trace contaminants must be incinerated. Membrane processes also have the potential for allowing toxic contaminants into the fuel product and degradation of the membrane by trace contaminants is possible.

U.S. Pat. No. 4,270,937 to Adler et al., owned by the assignee herein, discloses a comprehensive gas separation process for a feed gas containing methane and carbon dioxide together with impurities or contaminants pertinent herein. The Adler et al. process includes an initial liquid carbon dioxide absorption process for removing such contaminants from the feed gas stream as part of a liquid carbon-dioxide-enriched bottom product of the process, and it is observed that such processing may generally be used for separating such high boiling point components from relatively low boiling point gases and carbon dioxide.

While it is known to separate carbon dioxide from methane using a combination of compression and refrigeration, known processes have not further developed this basic technique. For example, U.S. Pat. No. 4,681,612 to O'Brien et al. utilizes the Adler et al. teaching to remove in bulk substantially all of the carbon dioxide present in a landfill gas together with the contaminants. This separation economically impairs any subsequent purification of the carbon dioxide and does not allow for economies in operating or equipment when a landfill gas containing a relatively minimum amount of contaminants is to be processed. Thus, the prior art has not taken full advantage of the contaminant separation capability of carbon dioxide, and therefore has not efficiently utilized refrigeration and compression to effect separation of such products. Consequently, refrigeration methods for separating methane from landfill or other gases having a high carbon dioxide content have been regarded generally as being economically unattractive.

In view of the prior art, it is evident that a cost effective process for recovering both a methane-rich fuel product and a highly pure carbon dioxide product from landfill gas, and for concentrating toxic impurities present in landfill gas at trace concentrations for efficient disposal, is desirable.

SUMMARY OF THE INVENTION

It has now been discovered that carbon dioxide separation factors for most landfill gas contaminants enable substantial removal of the contaminants using a relatively small proportion of the carbon dioxide present in the gas. The carbon dioxide containing the contaminants may be separated as a contaminant or spent absorbent stream in an absorption process and flared using the methane present in the stream.

The amount or concentration of methane in the contaminant stream is reduced in accordance with the invention, and, if necessary, additional methane may be added to the stream to effect flaring. In such a case, methane may be added by combining the flare stream with a flow of unprocessed landfill gas containing unprocessed methane gas. This is economical because the methane contained in the landfill gas is inexpensive since it has not been separation processed and there is no need to pressurize the methane containing landfill gas since the flaring is done at atmospheric pressure.

A methane enriched product stream also containing carbon dioxide and lighter gas constituents is withdrawn from the absorption process. The carbon dioxide and other constituents present in the methane product stream may be separated to provide a pipeline gas product or a liquified natural gas ("LNG") product as discussed more fully below.

A carbon dioxide enriched product stream also containing methane and lighter gas constituents is also withdrawn from the absorption process. The further processing and/or recovery of carbon dioxide is facilitated by the gross reduction of the amount of contaminants present since about 90% of the contaminants are removed by the initial separation of the contaminant or spent absorbent stream. In other words, the further carbon dioxide processing, i.e. food grade purification, is simplified by the prior elimination of most contaminants. This also tends to remove certain of the restrictions on alternative further processing techniques and may enable economic alternative processing such as crystallization or distillation.

The absorption process may be performed in one or two absorber columns or vessels. In a single column process, the methane product is withdrawn from the top of the column, the carbon dioxide product is withdrawn as a side stream from an intermediate location along the column height having the desired carbon dioxide purity, and the spent absorbent is withdrawn from the bottom of the column. In a two column process, the spent absorbent is withdrawn from the bottom of the first column, and a combined overhead intermediate or transfer product enriched in methane and carbon dioxide is withdrawn from the top of the first column. The combined intermediate product is introduced into the second column for separation of the carbon dioxide and methane, the methane product is withdrawn from the top of second column and a purified carbon dioxide product is withdrawn from the bottom of the second column.

The concentration of methane in the methane product from the absorption system may be selected in accordance with specific products to be produced and/or recovered. For example, the methane concentration may be maintained at an intermediate range (e.g. about 65 to 85 mole percent methane) to provide a feed stream to a methanol production process. Alternatively, the methane product stream from the absorption system may be further concentrated using a variety of processes as discussed below.

The methane product from the absorption system may be purified by a fine or final carbon dioxide removal using processing such as physical absorption, chemical absorption as with amines or hot potassium carbonate, membrane separation as shown in U.S. Pat. No. 4,681,612, adsorption with the carbon dioxide being adsorbed onto the surface of a solid such as a molecular sieve, or freezing the carbon dioxide onto a recovery surface in an alternating freeze/melt type process. The further purified methane product obtained in the fine carbon dioxide removal process may be used as a pipeline gas product or as an LNG product depending upon the degree of purification.

In the production of LNG, the fine carbon dioxide removal is preferably done using methanol absorption of the carbon dioxide to provide a carbon dioxide free, methane and nitrogen feed for liquefaction. The liquefaction may be done in a conventional manner to produce a liquid methane bottom product and an overhead product containing methane and nitrogen. The liquefaction overhead product is substantially free of carbon dioxide and contains a sufficient concentration of methane to enable its use as a fuel for the generators and compressors required in the processing of the landfill gas as described above.

In accordance with the invention, it is also contemplated to use the overhead liquefaction product to strip the carbon dioxide from the spent methanol absorbent. The regenerated methanol is recycled back to the methanol absorber from the stripping process and an overhead stripper product is formed containing the overhead liquefaction product together with the stripped carbon dioxide. The overhead stripper product may be used to fuel the generators and compressors as described above. In most cases, the remaining methane in the overhead liquefaction product or the overhead stripper product is sufficient to provide the energy required for the landfill gas recovery process or such may be achieved with selected processing variables.

DETAILED DESCRIPTION OF THE DRAWINGS

Figure 1:
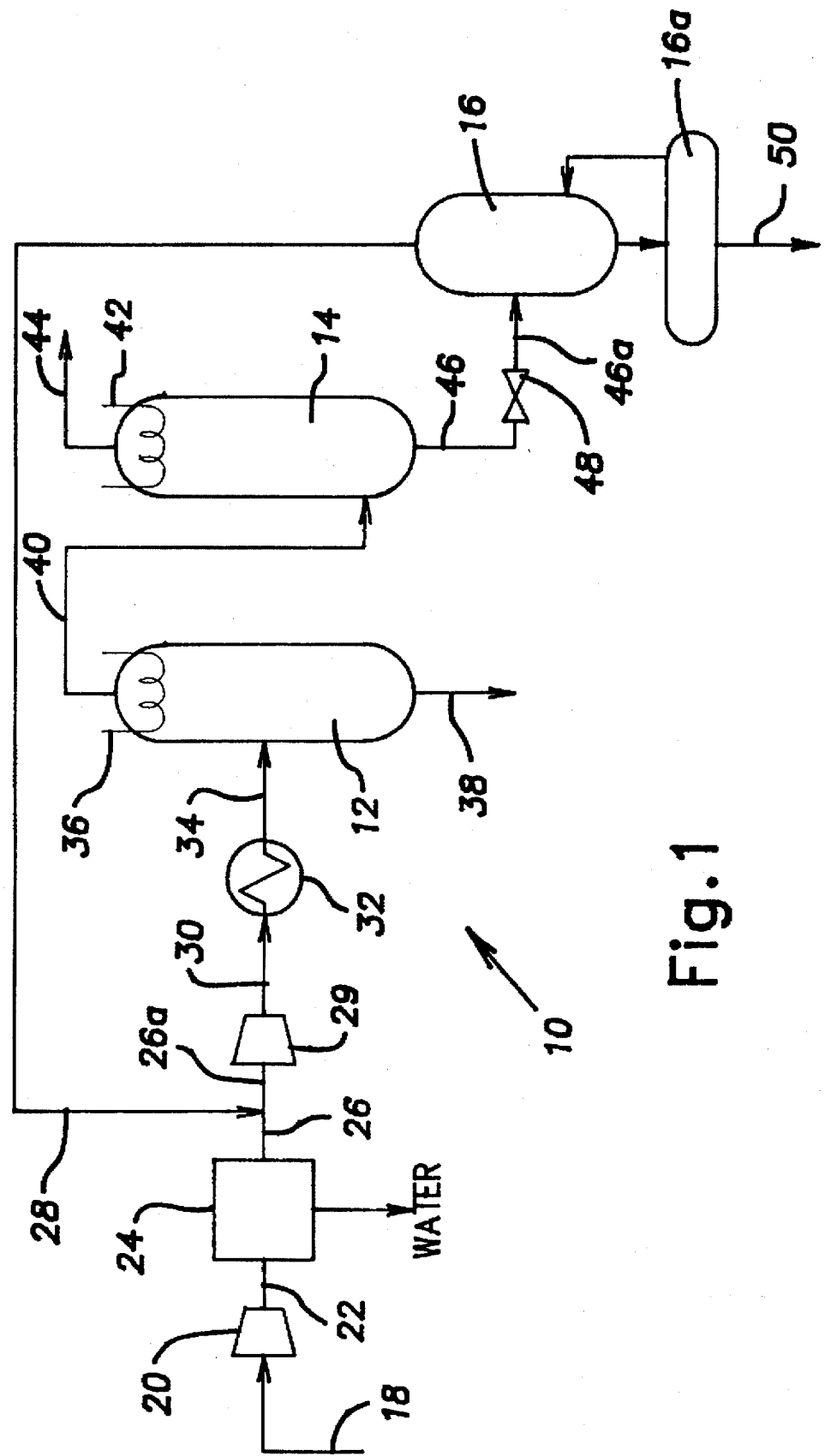
FIG. 1 is a general flow diagram for a system in which the absorption is performed in two successive columns to produce an absorption system methane product, a spent absorbent or contaminant stream and a carbon dioxide enriched product, the latter being stripped to provide a food grade carbon dioxide product and a recycle stream.

Referring to FIG. 1, an absorption system 10 includes as it major elements a first absorption column 12 and a second absorption column 14. Optionally, a stripper 16 may be used if an enriched carbon dioxide product is to be recovered with recycle of additional separated methane.

In the system 10, the columns 12 and 14 are connected in series and operating conditions are particularly selected so that substantially all of the contaminants are removed as a bottom product from column 12 with a minimized amount of carbon dioxide to achieve such separation. A methane enriched overhead product is removed from column 14 by primarily separating methane from carbon dioxide. Also, a carbon dioxide enriched bottom product that is substantially free of contaminants is removed from column 14 so that it is only necessary to strip methane and nitrogen as well as lighter constituents in order to form food grade carbon dioxide. The operation of the system 10 is described below in greater detail.

Landfill feed gas collected in a known manner from a landfill is introduced into the system 10 through line 18 and compressed to a pressure of about 210 psia by compressor 20. The compressed gas passes via line 22 to a drier 24 for removal of moisture normally contained in landfill gas. The compressed and dried gas passes from drier 24 through line 26 for combination with a recycle flow of methane in line 28, the recycle flow being more fully described below. The combined gas and methane recycle flow continues through line 26a to a second compressor 29 wherein its pressure is further increased, and it then passes via line 30 to heat exchanger 32 for cooling to near the dew point temperature of carbon dioxide. The dried, pressurized and cooled gas flows through line 34 into absorption column 12.

The contaminants in the landfill gas flowing into the column 12 are absorbed by carbon dioxide derived from the landfill gas feed stream. (Alternate sources of carbon dioxide may be used in whole or in part, but economics presently do not favor the same.) A condenser 36 assures a suitable absorbent flow of carbon dioxide down the column 12 and carbon dioxide spent absorbent containing most of the contaminants is withdrawn from the bottom of the column via line 38. The column 12 is operated at a relatively high temperature, e.g. warmer than about −30° F., in order to effect the required separation of the contaminants using a minimized amount of carbon dioxide. This also achieves the separation with a correspondingly minimized amount of energy and less expensive carbon steel. Such operation is based on applicant's discovery of the effectiveness of carbon dioxide to remove most landfill gas contaminants, e.g. 90% of the contaminants, at relatively low flows. More particularly, the K factor for most contaminants has been found to be sufficiently small to enable contaminant removal by absorption processing with carbon dioxide flows equal to about one-third of the carbon dioxide contained in the landfill gas feed stream. In most applications, the amount of carbon dioxide used as absorbent will range from about 25% to about 35% of the carbon dioxide originally present in the landfill gas feed stream.

A combined overhead intermediate or transfer product enriched in methane and carbon dioxide is withdrawn from the top of the column 12 via line 40 and introduced into column 14 for further absorption separation of methane and carbon dioxide. A further flow of carbon dioxide absorbent is provided in column 14 by condenser 42.

A methane enriched overhead absorption product is withdrawn from column 14 through line 44 and a carbon dioxide enriched bottom product is withdrawn from the bottom of column 14 through line 46. This flow of carbon dioxide in line 46 is substantially free of contaminants and may be vented to the atmosphere.

If a food grade carbon dioxide product is to be recovered, the pressure of the stream flowing in line 46 may be reduced by valve 48 and the lower pressure stream may be passed via line 46a to the stripper 16 having a reboiler 16a. The methane enriched overhead product from the stripper 16 is recycled to the process through line 28. Depending upon the type of contaminants present in the landfill feed gas, a carbon dioxide enriched stream withdrawn from the reboiler 16a via line 50 may be suitable for use as food grade carbon dioxide or may require further purification as described below.

As used herein, food grade carbon dioxide contains at least 99.0% carbon dioxide and less than the following concentrations of contaminants in parts per million (ppm) or parts per billion (ppb):

| | |
|---|---|
| 1 ppm | hydrogen sulfide |
| 1 ppm | of other sulfur containing compounds |
| 20 ppm | paraffinic hydrocarbons such as methane, propane, butane, pentane, hexane etc. |
| 10 ppm | Freon-12, dichlorodifluoromethane |
| 100 ppb | vinyl chloride |
| 100 ppb | methyl chloride |
| 100 ppb | of other chlorine containing compounds |
| 50 ppb | benzene, toluene, xylenes (BTX's) |

The USP definition of food grade carbon dioxide includes carbon monoxide, nitric oxide, nitrogen dioxide and ammonia limitations not pertinent herein since such contaminants are not present in landfill gas. In accordance with the present process, carbon dioxide purities as high as 99.99% may be achieved.

Figure 2:
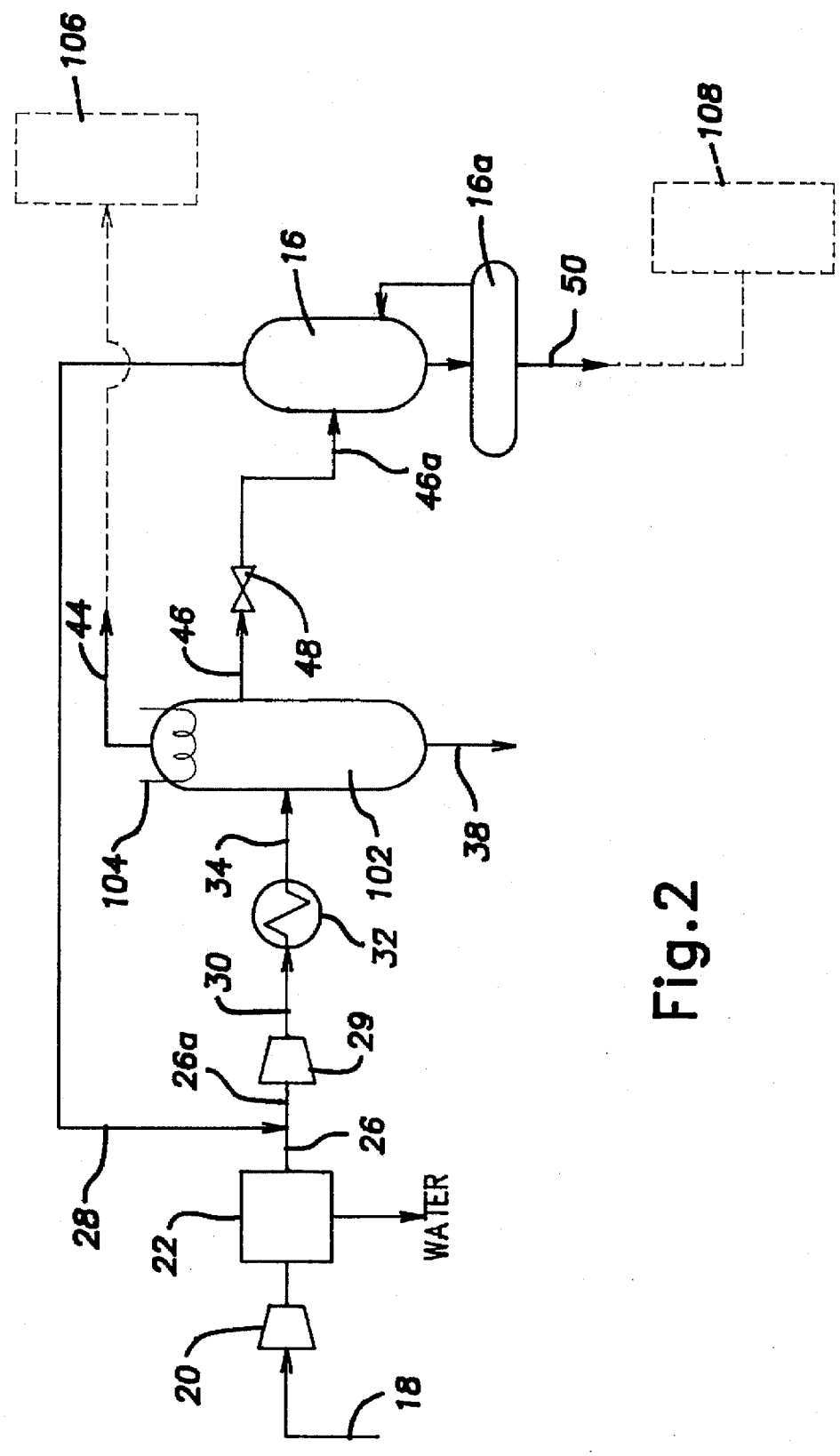
FIG. 2 is a general flow diagram for a system in which the absorption is performed in a single column.

Referring to FIG. 2, a general flow diagram is shown for an absorption system 100 including a single absorption column 102. In this embodiment, the same reference numerals as used in the first embodiment are used for like elements and/or lines containing like streams.

As indicated in FIG. 2, absorption system 100 is identical with system 10 except for the use of a single column 102 to replace columns 12 and 14. The flow of carbon dioxide absorbent is provided by the condenser 104 at the top of the column 102.

In comparison with columns 12 and 14, the column 102 includes a similar total number of theoretical stages to effect the same operations. Further, the carbon dioxide enriched product contained in line 46 is withdrawn as a side stream from the column 102 at a point of suitable concentration. In this manner, the same minimized amount of carbon dioxide absorbent is used to remove the contaminants as in the absorption system 10. However, the column 12 operates at a relatively higher temperature and therefore uses a lesser amount of energy to effect the separation of the bulk of the contaminants.

The following Examples 1 and 2, are based upon a Hysim process simulator by Hyprotech Ltd. of Canada. The examples compare the recovery of landfill gas feed streams that each contain about 49% methane and 48% carbon dioxide and respectively contain the contaminants indicated below.

The processing of the landfill gas feed streams was simulated using the system 100 of FIG. 2 having the single absorption column 102 and stripper 16 with recycle. The compositions of pertinent streams including feed and product streams are reported below in Tables 1 and 2 for Examples 1 and 2 respectively.

TABLE 1[1]

| Stream | 18 | 34 | 38 | 46a | 28 | 44 | 50 |
|---|---|---|---|---|---|---|---|
| Molar Flow[2] | 509 | 577 | 83 | 200 | 73 | 293 | 127 |
| Methane | 48.8 | 48.9 | 13.3 | 13.6 | 37.4 | 83.1 | 5E-6 |
| CO2 | 47.8 | 50.3 | 86.5 | 86.3 | 62.3 | 15.4 | 100.0 |
| Nitrogen | 0.9 | 0.9 | 0.1 | 0.1 | 0.3 | 1.6 | 0.0 |
| H2S | 0.5 | 0.5 | 1.1 | 0.9 | 0.5 | 0.1 | 1.1 |
| M-Mercaptan | 9.8 | 8.6 | 59.5 | 0.0 | 0.0 | 0.0 | 0.0 |
| Refrig-40[3] | 0.4 | 0.3 | 2.3 | 0.0 | 0.0 | 0.0 | 0.1 |
| VinylCl[4] | 3.9 | 3.5 | 23.8 | 0.0 | 0.0 | 0.0 | 0.1 |
| ClC2[5] | 2.0 | 1.7 | 12.0 | 0.0 | 0.0 | 0.0 | 0.0 |
| C11—Cl[6] | 24.4 | 21.5 | 148.5 | 0.0 | 0.0 | 0.0 | 0.0 |
| Cl3—C2=[7] | 6.1 | 5.4 | 37.5 | 0.0 | 0.0 | 0.0 | 0.0 |
| Refrig-12[8] | 7.9 | 7.0 | 38.0 | 4.4 | 0.8 | 0.0 | 6.4 |

TABLE 1[1]-continued

| Stream | 18 | 34 | 38 | 46a | 28 | 44 | 50 |
|---|---|---|---|---|---|---|---|
| Acetone | 34.2 | 30.2 | 208.4 | 0.0 | 0.0 | 0.0 | 0.0 |
| Benzene | 2.0 | 1.7 | 12.0 | 0.0 | 0.0 | 0.0 | 0.0 |
| Toluene | 68.2 | 60.2 | 415.7 | 0.0 | 0.0 | 0.0 | 0.0 |
| p-Xylene | 24.4 | 21.5 | 148.5 | 0.0 | 0.0 | 0.0 | 0.0 |
| Propane | 4.9 | 5.1 | 10.6 | 9.0 | 6.5 | 1.0 | 10.4 |
| n-Butane | 4.9 | 4.4 | 22.9 | 3.1 | 0.7 | 0.0 | 4.5 |
| n-Pentane | 14.5 | 12.8 | 88.6 | 0.0 | 0.0 | 0.0 | 0.0 |
| n-Hexane | 14.5 | 12.8 | 88.6 | 0.0 | 0.0 | 0.0 | 0.0 |
| H2O | 2.6 | 0.0 | 0.0 | 0.0 | 0.0 | 0.0 | 0.0 |

[1]All concentrations reported in parts per million (ppm) except methane, carbon dioxide, nitrogen and water which are reported as mole percent.
[2]lb mole/hr
[3]Chloromethane
[4]Vinyl Chloride
[5]Chloroethane
[6]Methylene Chloride
[7]Trichloroethene
[8]Dichlorodifluoromethane

TABLE 2[1]

| Stream | 18 | 34 | 38 | 46a | 28 | 44 | 50 |
|---|---|---|---|---|---|---|---|
| Molar Flow[2] | 509 | 587 | 62 | 228 | 83 | 297 | 145 |
| Methane | 48.8 | 48.6 | 13.2 | 13.5 | 37.1 | 83.1 | 5E-6 |
| CO2 | 47.8 | 50.5 | 86.5 | 86.4 | 62.5 | 15.4 | 100.0 |
| Nitrogen | 0.9 | 0.9 | 0.1 | 0.1 | 0.3 | 1.6 | 0.0 |
| H2S | 0.5 | 0.5 | 1.1 | 0.9 | 0.5 | 0.1 | 1.1 |
| M-Mercaptan | 9.8 | 8.5 | 79.0 | 0.2 | 0.0 | 0.0 | 0.3 |
| Refrig-40 | 0.1 | 0.1 | 0.6 | 0.0 | 0.0 | 0.0 | 0.1 |
| VinylCl | 0.2 | 0.2 | 1.5 | 0.0 | 0.0 | 0.0 | 0.1 |
| ClC2 | 2.0 | 1.7 | 16.0 | 0.0 | 0.0 | 0.0 | 0.0 |
| Cl2—Cl | 24.5 | 21.1 | 198.9 | 0.0 | 0.0 | 0.0 | 0.0 |
| Cl3—C2= | 6.1 | 5.3 | 50.2 | 0.0 | 0.0 | 0.0 | 0.0 |
| Refrig-12 | 3.9 | 3.5 | 18.8 | 3.8 | 0.7 | 0.0 | 5.5 |
| Acetone | 34.2 | 29.6 | 279.1 | 0.0 | 0.0 | 0.0 | 0.0 |
| Benzene | 2.0 | 1.7 | 16.0 | 0.0 | 0.0 | 0.0 | 0.0 |
| Toluene | 68.2 | 59.1 | 556.6 | 0.0 | 0.0 | 0.0 | 0.0 |
| p-Xylene | 24.4 | 21.1 | 198.9 | 0.0 | 0.0 | 0.0 | 0.0 |
| Propane | 3.9 | 4.3 | 8.9 | 7.6 | 5.6 | 0.8 | 8.8 |
| n-Butane | 3.9 | 3.5 | 18.4 | 4.0 | 0.9 | 0.0 | 5.8 |
| n-Pentane | 14.5 | 12.6 | 118.3 | 0.1 | 0.0 | 0.0 | 0.2 |
| n-Hexane | 14.5 | 12.6 | 118.7 | 0.0 | 0.0 | 0.0 | 0.0 |
| H2O | 2.6 | 0.0 | 0.0 | 0.0 | 0.0 | 0.0 | 0.0 |

[1]All concentrations reported in parts per million (ppm) except methane, carbon dioxide, nitrogen and water which are reported as mole percent.
[2]lb mole/hr In Example 1, the dried feed gas contains about 49% carbon dioxide, 50% methane, 1% nitrogen and approximately 200 ppm of contaminants. For an absorber running at 700 psia, 52% of the feed carbon dioxide is recovered as food grade carbon dioxide and 30% of the feed carbon dioxide is used as absorbent. The remainder of the feed carbon dioxide remains with the methane product. The food grade carbon dioxide contains less than one part per billion of these contaminants which have boiling points above room temperature. The dried feed gas has a concentration of 180 ppm of these contaminants. Accordingly, the concentration of these high boiling contaminants is reduced over 100,000 fold from the feed in line 18 to the carbon dioxide product in line 50. Other high boiling contaminants will be removed to a similar extent. Contaminants having a boiling point below room temperature have concentrations of from a few parts per billion to a few parts per million in the food grade carbon dioxide.

In Example 2, the landfill gas feed has a lower concentration of certain of the more volatile contaminants such a methyl chloride (Refrig-40), vinyl chloride, propane, butane and Freon 12 (Refrig-12) in the feed. For this feed gas composition, 60% of the carbon dioxide is recovered as food grade carbon dioxide and 22% of the carbon dioxide is used as absorbent.

TABLE 3

| Feed to Carbon Dioxide Product Ratio | | |
|---|---|---|
| Contaminant | Example 1 | Example 2 |
| Hydrogen Sulfide (H$_2$S) | 0.5 | 0.5 |
| Methyl Mercaptan | 1,667 | 37.0 |
| Chloromethane (Refrig-40) | 5.7 | 1.2 |
| Vinyl Chloride (VinylCl) | 55.6 | 3.4 |
| Chloroethane (ClC$_2$) | >4,000 | >4,000 |
| Methylene Chloride (Cl$_2$—Cl) | >50,000 | >50,000 |
| Trichloroethene (Cl3—C2=) | >12,000 | >12,000 |
| Dichlorodifluoromethane (R-12) | 1.3 | 1.1 |
| Benzene | >4,000 | >4,000 |
| Toluene | >140,000 | >140,000 |
| Xylenes | >50,000 | >50,000 |
| Acetone | >70,000 | >70,000 |
| Methane | 100,000 | 100,000 |
| Propane | 0.5 | 0.5 |
| Butane | 1.1 | 0.7 |
| Pentane | 3,750 | 83.3 |
| Hexane | >30,000 | >30,000 |

Examples 1 and 2 illustrate the efficiency of the processing of the invention to minimize the amount of carbon dioxide used in the separation of the contaminants. These examples also show the ability of the practitioner to modify the processing streams to accommodate specific contaminants present in the landfill gas feed stream.

The efficiencies achieved in accordance with the present invention are further illustrated by direct comparison with the process of the above noted U.S. Pat. No. 4,681,612 to O'Brien et al. A simulated comparison of processing in accordance with Example 1 of the present invention and processing in accordance with the O'Brien patent to recover methane and food grade carbon dioxide in like amounts and purities assuming like landfill gas feed stream flows of 4.64 MMSCFD shows that the O'Brien process requires 36% more energy. That is, the O'Brien processing technique wherein the contaminants are absorbed using substantially all of the available carbon dioxide requires an additional 36% more energy to process essentially similar feeds and recover like amounts and purities of products. This is shown in the following comparison of cooling and energy requirements for the two processes.

| | Cooling Btu/hr | Work Horsepower |
|---|---|---|
| Refrigeration requirements in accordance with Example 1. | | |
| Cryogenic Distillation Condenser (condenser 104) | 1,353,000 | 525 |
| Additional Compression for Recycle Gas | | 63 |
| Total | 1,353,000 | 588 |
| Refrigeration requirements in accordance with O'Brien et al. | | |
| CO2 Purification Condenser (condenser 208) | 470,000 | 100 |
| Cryogenic Distillation Condenser (condenser 190) | 1,807,000 | 700 |
| Total | 1,917,000 | 800 |

The reduced energy requirement in accordance with the present invention is associated with the elimination of the separate carbon dioxide purification column (202) used in O'Brien et al. to separate the contaminants from all of the carbon dioxide present in the landfill gas feed stream and the refrigeration requirement of the separation. Such column and refrigeration requirement are eliminated by separating the contaminants with a lesser amount of carbon dioxide (e.g. 30% of the carbon dioxide originally present in the landfill gas feed stream) in the single column system or in the first column of the two column system in accordance with the inventive process. Energy savings are also associated with the cooling required to remove the relatively higher heat input into the bottom portion of the O'Brien et al. cryogenic distillation column (174). The higher heat input is due to the reduced methane volatility in the stripping section of such column as compared with stripper 16 of the present invention.

The multiple absorption column system 10 and the single absorption column system 100 may provide a food grade carbon dioxide product as described above. However, if the landfill gas feed stream contains high concentrations of the low boiling point contaminants, hydrogen sulfide (>0.5 ppm) or propane (>10 ppm), then the carbon dioxide product may require further processing to meet food grade specifications. In such a case, the carbon dioxide may be further purified using crystallization processing or adsorption processing with a carbon bed or zinc if substantial amounts of hydrogen sulfide are present to produce a food grade product and a carbon dioxide stream concentrated in contaminants. As shown in dotted line in FIG. 2, the carbon dioxide product in line 50 may be fed to a crystallization separation apparatus such as a triple point crystallization apparatus 108. Triple point crystallization is illustrated in detail in U.S. Pat. Nos. 4,623,372, 4,609,388, 4,581,052 and 4,270,937, all of which are owned by the assignee of this application.

The removal of butane and/or Freon-12 by crystallization processing enables the use of relatively low carbon dioxide absorbent flows, e.g. 25 to 35% of the carbon dioxide present in the landfill gas. Much higher flows of the available carbon dioxide (e.g. 40%) would otherwise be required in the absorption processing to remove high concentrations of such contaminants. Thus, crystallization processing may provide not only the advantageous removal of difficult contaminant species, but may also enable the continued economies of low absorbent flows in accordance with the invention.

In another application of the invention, the concentration of carbon dioxide in the methane product in line 44 may be retained at a relatively high level, e.g. 15 to 35 mole percent carbon dioxide, if the methane product stream is to be used as a synthesis gas for methanol production. In this instance, the carbon dioxide assists in the methanol production reactions. (*Encyclopedia of Chemical Technology*, Vol. 15, 1981, pp. 400.) An alternate extension of line 44 to a methanol production process 106 is shown in dotted line in FIG. 2.

Figure 3:
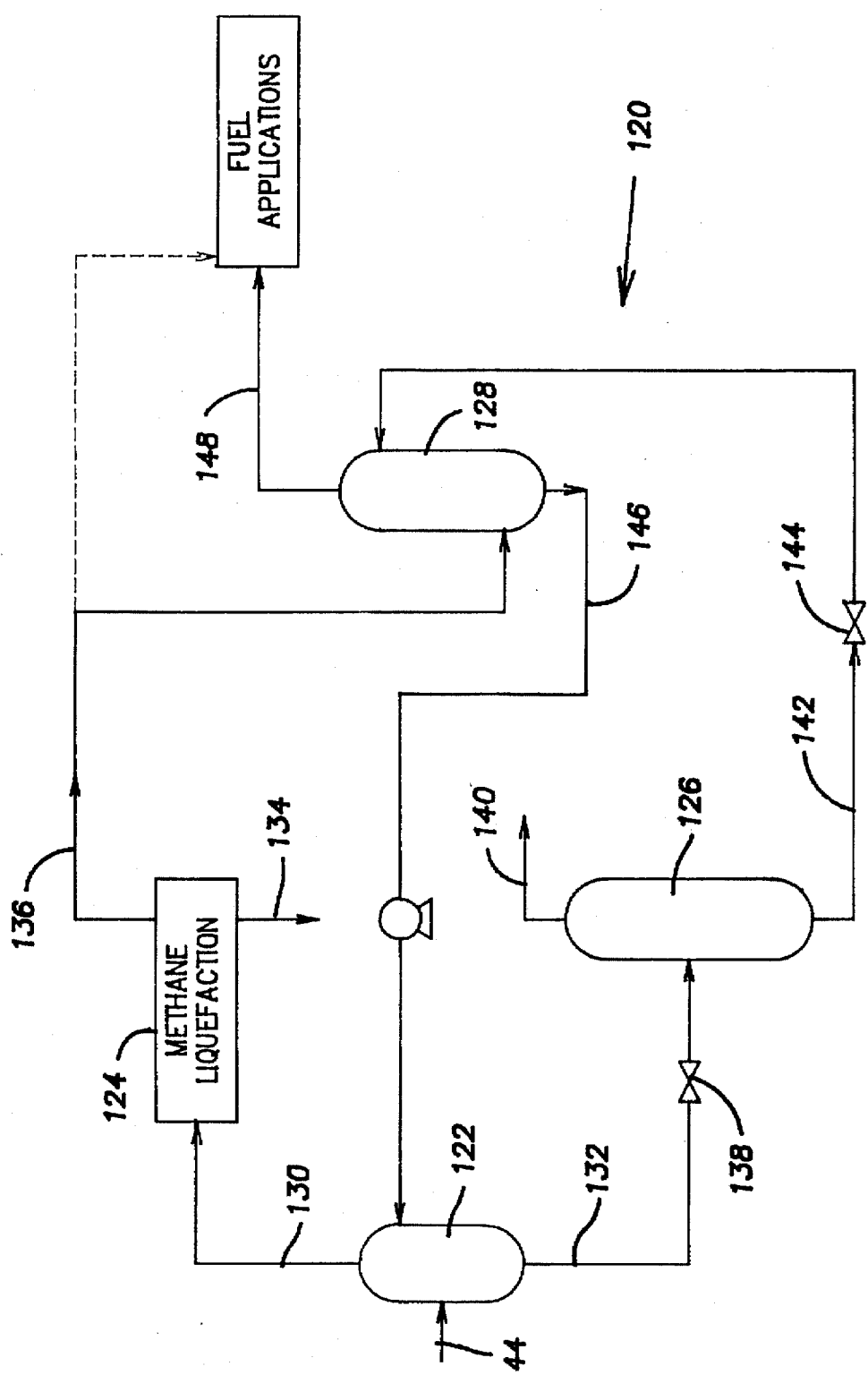
FIG. 3 is a general flow diagram for a fine carbon dioxide removal system including methanol absorption to separate carbon dioxide from methane and liquefaction to produce LNG wherein the liquefaction overhead product is used to strip the spent methanol absorbent and/or provide the fuel requirements for the system.

The methane product stream in line 44 may be further purified for use as a pipeline grade natural gas fuel or for the manufacture of LNG. To that end, the methane product from the absorption system 10 or 100 may be introduced into a fine or final carbon dioxide removal system 120 as shown in FIG. 3.

The fine carbon dioxide removal system includes as its major elements an absorber 122 for separating methane from carbon dioxide, a methane liquefaction apparatus 124, and a flash drum 126 for separating liquid spent absorbent to be regenerated in a stripper 128 and recycled to the process. The solvent used in the absorber 122 may be an alcohol such as methanol or a ketone such as methyl ethyl ketone, the use of methanol is illustrated herein. The fine carbon dioxide system 120 is described below in detail.

The methane product in line 44 is fed to the absorber 122 for contact with a methanol solvent for removal of the carbon dioxide from the methane. The methanol solvent washes the carbon dioxide from the methane gas in the absorber 122, and a carbon dioxide free methane feed gas is withdrawn from the top of the absorber through line 130 and passed to the methane liquefaction apparatus 124 for further processing as described below. The spent methanol solvent containing the dissolved carbon dioxide is withdrawn from the bottom of the absorber 122 through line 132 for recycle of its methane component and solvent regeneration.

The carbon dioxide free product or methane feed gas in line 130 is introduced into the liquefaction apparatus 124 for separation of lighter constituents and liquefaction of the methane. Liquefaction may be provided using either compression and expansion system or a cascade system, the latter being preferred presently. (Ringler, Liquefied Natural Gas and Nonconventional Gas Storage, *Gas Engineers Handbook*, Chapter 4, 1965.) A liquid methane or LNG product is withdrawn from the apparatus 124 through line 134 for storage or shipment. A separated liquefaction gas stream consisting of nitrogen and methane is also withdrawn from the apparatus 124 through line 136. As described below, the liquefaction gas stream may be use as a fuel or as a stripping gas in stripper 128 and then as a fuel. In either case, the liquefaction gas stream contains sufficient methane to enable fuel applications and it is substantially free of carbon dioxide and undesirable contaminants.

Returning to the operation of the absorber 122, spent absorbent in line 132 is passed through an expansion valve 138 to reduce the pressure thereof. The spent methanol absorbent then enters flash drum 126 where dissolved methane is flashed out of the solvent and recycled via line 140 to the beginning of the process. The liquid solvent containing product is withdrawn from the bottom of the drum 126 through line 142 and its pressure is reduced as it passes through expansion valve 144. The liquid solvent is introduced into the top of the stripper 128 which operates at slightly above atmospheric pressure, e.g. 18 to 20 psia. The liquefaction gas stream in line 136 is introduced into the bottom of the .stripper 128 for stripping carbon dioxide contained in the spent absorbent. The regenerated absorbent is removed from the bottom of the stripper through line 146 and pumped back to the top of the absorber 122. The stripping gas leaves the top of the stripper 128 through line 148 and it is usable in fuel applications since it is substantially free of contaminants and contains methane and carbon dioxide in suitable proportions. Accordingly, the liquefaction gas stream in line 136 may be used directly in fuel applications as shown in dotted outline in FIG. 3 or it may first be used as a stripping gas to regenerate the methanol absorbent.

The processing of the methane product stream in line 44 is simulated to obtain the following results. The component compositions are reported in mole fractions.

TABLE 4

| Stream | 44 | 132 | 142 | 140 | 136 | 148 | 146 |
|---|---|---|---|---|---|---|---|
| Temp.[1] | −74 | −50 | −49 | −49 | 5 | −78 | −84 |
| Press.[2] | 700 | 700 | 220 | 220 | 20 | 18 | 20 |
| Flow[3] | 294 | 280 | 272 | 8.23 | 64.5 | 111 | 226 |
| Methane | .831 | .035 | .011 | .817 | .935 | .568 | 99E-5 |
| Nitrogen | .015 | 93E-6 | 5E-6 | .003 | .065 | .038 | 5E-6 |
| Methanol | 0 | .803 | .827 | 0 | 0 | 70E-6 | .999 |
| CO2 | .153 | .161 | .161 | .180 | 10E-6 | .394 | 56E-6 |

[1]Degrees Fahrenheit
[2]psia
[3]lb mole/hr

The LNG product withdrawn through line 134 is substantially pure methane suitable for storage or fuel applications. (It contains 99.9% methane, 0.1% nitrogen and 0.65 ppm carbon dioxide.) The liquefaction gas product in line 136 contains about 93% methane, 6.5% nitrogen and trace amounts of carbon dioxide. This gas may be used directly as a fuel for compression and refrigeration requirements in the process as shown by the dotted line alternative extension of line 136 to fuel applications, or it may be used as a stripping gas to regenerate the methanol in stripper 128. In the latter case, the gas product in line 148 from the top of the stripper 128 may still be used in fuel applications since it is substantially free of contaminants and contains about 57% methane, 39% carbon dioxide and 4% nitrogen.

The top product withdrawn in line 140 from the flash drum 126 is free of methanol and contains about 82% methane and 18% carbon dioxide. It is therefore recycled back to the process for recovery of the constituents therein.

What is claimed is:

1. A process for separating carbon dioxide from a landfill gas feed stream containing carbon dioxide, methane and trace contaminants of relatively higher boiling gases, comprising the steps
    compressing the landfill gas feed stream and removing water therefrom to produce a dehydrated gas stream containing said methane, carbon dioxide and trace contaminants,
    introducing said dehydrated gas stream into an absorption column means for absorbing said contaminants with a carbon dioxide absorbent primarily comprising said carbon dioxide present in said landfill gas stream,
    withdrawing from said absorption column means, at a first location, a spent absorbent stream containing no more than about 35% of the carbon dioxide contained in the landfill gas feed stream and substantially all of said gas contaminants, withdrawing from said absorption column at a second location above said first location, a carbon dioxide product stream substantially free of contaminants containing a substantial portion of the carbon dioxide originally present in said landfill gas feed stream, and
    also withdrawing from said absorption column means a methane product stream substantially free of said contaminants and containing most of the methane originally contained in said landfill gas feed stream.

2. The process of claim 1, wherein said spent absorbent stream contains from about 25 to about 35% of the carbon dioxide originally contained in said landfill gas feed stream.

3. The process of claim 1, including combining the spent absorbent stream with additional landfill gas to form a combined flare stream containing sufficient methane to support combustion and flaring the combined flare stream.

4. The process of claim 1, including the further step of forming food grade carbon dioxide by separating the carbon dioxide in said carbon dioxide product stream from only methane and other relatively lower boiling contaminants.

5. The process of claim 1, wherein said carbon dioxide product stream is a side product stream and said methane product stream is a top product stream containing most of the methane; and including the further stem of separating the carbon dioxide and methane of said side product stream to form a recycle methane enriched stream that is returned to the process.

6. The process of claim 5, wherein said step of separating the carbon dioxide and methane of the said side product stream includes stripping the methane from the carbon dioxide to form said recycle methane enriched stream and a food grade carbon dioxide product.

7. The process of claim 5, including the further step of forming food grade carbon dioxide by separating the carbon dioxide from only methane and other relatively higher boiling contaminants.

8. The process of claims 4, wherein the step of forming food grade carbon dioxide includes separating the carbon dioxide from methane and other relatively higher boiling contaminants by crystallization.

9. The process of claim 8, wherein the crystallization step is performed at the triple point conditions of carbon dioxide.

10. The process of claim 2, including the further step of reforming said methane enriched product stream to provide a synthesis gas and converting the synthesis gas to methanol.

11. The process of claim 1, wherein said absorption column means comprise first and second absorbers, and including the further steps of withdrawing from said first absorber a combined overhead product stream enriched in methane and containing carbon dioxide to be recovered, introducing said overhead product stream as a feed into said second absorber, withdrawing from said second absorber said methane product stream and said carbon dioxide product stream.

12. The process of claim 11, including the further step of forming food grade carbon dioxide by processing said carbon dioxide product stream to separate carbon dioxide from only methane and other relatively higher boiling contaminants.

13. The process of claim 5 or 11, including the further step of removing additional carbon dioxide from said methane product stream by contacting it with a second absorbent to form a second methane product stream suitable for liquefaction and a second spent absorbent stream containing carbon dioxide removed from said first mentioned methane product stream, liquefying said second methane product stream to form a liquid methane product and an overhead liquefaction gas stream substantially free of carbon dioxide and contaminants, and contacting said second spent absorbent with said overhead liquefaction gas to regenerate the second absorbent and form a stripping gas containing the carbon dioxide stripped from the second spent absorbent stream.

14. The process of claim 13, wherein said stripping gas is substantially free of contaminants and contains a sufficient amount of methane to enable its use as an engine fuel, and said stripping gas is used to provide compression and cooling required in the process.

15. The process of claim 14, wherein said second absorbent is methanol.

16. The process of claim 5 or 11, including the further step of removing additional carbon dioxide from said methane product stream by contact with a second absorbent to form a second methane product stream suitable for liquefaction and a second spent absorbent stream containing carbon dioxide removed from said first mentioned methane product stream, liquefying said second methane product stream to form a liquid methane product and an overhead liquefaction gas stream substantially free of carbon dioxide and contaminants, said overhead liquefaction gas stream being substantially free of contaminants and containing sufficient methane to enable its use as an engine fuel, and said overhead liquefaction gas stream is used to provide compression and cooling required in the process.

17. The process of claim 16, wherein said absorbent is methanol.

18. A process for separating carbon dioxide from a landfill gas feed stream containing carbon dioxide, methane and trace contaminants of relatively higher boiling gases comprising the steps of:
    compressing the landfill gas feed stream and removing water therefrom to produce a dehydrated gas stream containing said methane, carbon dioxide and trace contaminants, introducing said dehydrated gas stream into an absorption column for absorbing said contaminants with a carbon dioxide absorbent comprising a portion of said carbon dioxide present in said landfill gas stream, and withdrawing from said absorption column, at a first location, a spent absorbent stream comprising no more than about about 35% of the carbon dioxide contained in the landfill gas feed stream and substantially all of said gas contaminants, withdrawing from said absorption column, at a second location above said first location, a side product stream containing a substantial portion of the carbon dioxide originally contained in said landfill gas feed stream, and withdrawing from said absorption column a methane product stream containing most of the methane originally contained in the landfill gas feed stream.

19. The process of claim 18, wherein said spent absorbent stream contains from about 25 to about 35% of the carbon dioxide originally contained in said landfill gas feed stream.

20. The process of claim 19, wherein said contaminants comprise at least one member selected from the group consisting of toluene, trichloroethylene, methyl ethyl ketone, acetone, methyl mercaptan, vinyl chloride, methyl chloride, Freon-12 and Freon-22, and said spent absorbent stream contains a flow of carbon dioxide just sufficient to achieve an L/KV ratio greater than one for the one or more contaminants present in the landfill gas feed stream.

21. The process of claim 18, including the further step of forming food grade carbon dioxide by separating the carbon dioxide from substantially only methane and other relatively higher boiling contaminants.

22. The process of claims 21, wherein the step of forming food grade carbon dioxide includes separating the carbon dioxide from methane and other relatively higher boiling contaminants by crystallization.

23. The process of claim 22, wherein the crystallization step is performed at the triple point conditions of carbon dioxide.

24. The process of claim 18, including the further step of reforming said methane enriched product stream to provide a synthesis gas and converting the synthesis gas to methanol.

25. The process of claim 20, including the further step of removing additional carbon dioxide from said methane product stream by contact with a second absorbent to form a second methane product stream suitable for liquefaction and a second spent absorbent stream containing carbon dioxide removed from said first mentioned methane product stream, liquefying said second methane product stream to form a liquid methane product and an overhead liquefaction gas stream substantially free of carbon dioxide and contaminants, and contacting said second spent absorbent with said overhead liquefaction gas to regenerate the second absorbent and form a stripping gas containing the carbon dioxide stripped from the second spent absorbent.

26. The process of claim 25, wherein said stripping gas is substantially free of contaminants and contains a sufficient amount of methane to enable its use as an internal combustion engine fuel, and said stripping gas is used to provide compression and cooling required in the process.

27. A process for separating carbon dioxide from a landfill gas feed stream containing carbon dioxide, methane and trace contaminants of relatively higher boiling gases comprising the steps of:

compressing the landfill gas feed stream and removing water therefrom to produce a dehydrated gas stream containing said methane, carbon dioxide and trace contaminants, introducing said dehydrated gas stream into a first absorption column for absorbing said contaminants with a carbon dioxide absorbent comprising a portion of said carbon dioxide present in said landfill gas feed stream, withdrawing from said first absorption column absorber, at a first location, a spent absorbent stream comprising no more than about about 35% of the carbon dioxide contained in the landfill gas feed stream and substantially all of said gas contaminants, and a combined overhead product stream enriched in methane and containing carbon dioxide to be recovered, introducing said combined overhead product stream from said first absorption column, as a feed, into a second absorption column to separate carbon dioxide from methane using a carbon dioxide absorbent to form a bottom product containing methane and a substantial portion of the carbon dioxide originally present in the landfill gas feed stream and a methane product stream substantially free of said contaminants and containing most of the methane originally present in the landfill gas stream.

28. The process of claim 27, wherein said spent absorbent stream contains from about 25 to about 35% of the carbon dioxide originally contained in said landfill gas feed stream.

29. The process of claim 28, wherein said contaminants comprise at least one member selected from the group consisting of toluene, trichloroethylene, methyl ethyl ketone, acetone, methyl mercaptan, vinyl chloride, methyl chloride, Freon-12 and Freon-22, and said spent absorbent stream contains a flow of carbon dioxide just sufficient to achieve an L/KV ratio greater than one for the one or more contaminants present in the landfill gas feed stream.

30. The process of claim 27, including the further step of forming food grade carbon dioxide by separating the carbon dioxide from only methane and other relatively higher boiling contaminants.

31. The process of claim 27, including the further step of removing additional carbon dioxide from said methane product stream by contact with a second absorbent to form a second methane product stream suitable for liquefaction and a second spent absorbent containing carbon dioxide removed from said first mentioned methane product stream, liquefying said second methane product stream to form a liquid methane product and an overhead liquefaction gas stream substantially free of carbon dioxide and contaminants, and contacting said second spent absorbent with said overhead liquefaction gas to regenerate the absorbent and form a stripping gas containing the carbon dioxide stripped from the second spent absorbent.

32. The process of claim 31, wherein said stripping gas is substantially free of contaminants and contains a sufficient amount of methane to enable its use as an engine fuel, and said stripping gas is used to provide substantially all of the compression and cooling required in the process.

33. The process of claim 1, wherein said carbon dioxide product stream contains a majority of the carbon dioxide originally present in said landfill gas stream.

* * * * *